(12) United States Patent
Stark

(10) Patent No.: US 9,149,057 B2
(45) Date of Patent: *Oct. 6, 2015

(54) ENHANCED BIOAVAILABLE IODINE MOLECULES

(75) Inventor: Peter A. Stark, Inver Grove Heights, MN (US)

(73) Assignee: Zinpro Corporation, Eden Prairie, MN (US)

( * ) Notice: Subject to any disclaimer, the term of this patent is extended or adjusted under 35 U.S.C. 154(b) by 859 days.

This patent is subject to a terminal disclaimer.

(21) Appl. No.: 13/037,716

(22) Filed: Mar. 1, 2011

(65) Prior Publication Data

US 2012/0225161 A1 Sep. 6, 2012

(51) Int. Cl.
| | | |
|---|---|---|
| A23L 1/30 | (2006.01) |
| A23K 1/175 | (2006.01) |
| A23K 1/16 | (2006.01) |
| A23K 1/18 | (2006.01) |
| C07C 229/76 | (2006.01) |
| C07F 3/06 | (2006.01) |
| C07F 13/00 | (2006.01) |
| C07F 15/02 | (2006.01) |

(52) U.S. Cl.
CPC .............. *A23K 1/1758* (2013.01); *A23K 1/1634* (2013.01); *A23K 1/175* (2013.01); *A23K 1/1813* (2013.01); *C07C 229/76* (2013.01); *C07F 3/06* (2013.01); *C07F 13/005* (2013.01); *C07F 15/025* (2013.01)

(58) Field of Classification Search
CPC .. C07C 229/64; A23K 1/1813; A23K 1/1758; A23K 1/1634; A23K 1/175; C07F 13/005; C07F 3/06
USPC ...................... 426/618, 648; 556/50, 134, 148
See application file for complete search history.

(56) References Cited

U.S. PATENT DOCUMENTS

| | | |
|---|---|---|
| 2,281,612 A | 5/1942 | Witte |
| 3,950,372 A | 4/1976 | Abdel-Monem |
| 4,021,569 A | 5/1977 | Abdel-Monem |
| 4,039,681 A | 8/1977 | Abdel-Monem |
| 4,900,561 A | 2/1990 | Abdel-Monem et al. |
| 4,948,594 A | 8/1990 | Abdel-Monem et al. |
| 5,061,815 A * | 10/1991 | Leu ............................... 556/118 |
| 7,704,521 B2 | 4/2010 | Stark et al. |
| 7,846,471 B2 | 12/2010 | Stark et al. |
| 2003/0171598 A1 | 9/2003 | Zeng et al. |

OTHER PUBLICATIONS

Paulikova et al "Iodine Toxicity in Ruminants", Vet. Medicine-Czech, 47, 2002(12); 343-350.*
International Search Report, mailed May 2, 2012, PCT/US2012/026246, Applicant: Zinpro Corporation (6 pages).

* cited by examiner

*Primary Examiner* — Jyoti Chawla
(74) *Attorney, Agent, or Firm* — McKee, Voorhees & Sease, PLC

(57) ABSTRACT

This invention relates to supplementation of the diets of domesticated animals (livestock and poultry) with iodine in an enhanced bioavailable manner, that is to say the iodine is more available to the animal than when using conventional sources of iodine, such as calcium iodate. The supplementary compound are alpha amino acid metal iodide complexes.

4 Claims, No Drawings

ENHANCED BIOAVAILABLE IODINE MOLECULES

BACKGROUND OF THE INVENTION

This invention relates to supplementation of the diets of domesticated animals (livestock and poultry) with iodine in an enhanced bioavailable manner, that is to say the iodine is more available to the animal than when using conventional sources of iodine, such as calcium iodate. The supplementary compound are alpha amino acid metal iodide complexes.

It is well known that domesticated animals (livestock and poultry) are in need of bioavailable metal or mineral supplements, essential amino acids, and also are in need of iodine for healthy animal nutrition.

Iodine is a key component of hormones produced by the thyroid gland. The thyroid is responsible for growth, brain development and the rate at which animals burn energy. Two of the most common sources of iodine used in animal nutrition and therefore used in supplementing animal diets are calcium iodate ($CaIO_3$) and ethylenediamine dihydoiodide (EDDI). One test of the efficiency of effective metabolization of the iodine source by an animal is measuring blood serum levels of iodine after ingesting of the nutrient material.

In the animal feed industry it is known that insufficient availability of iodine to the animal can result in conditions such as goiters, reproductive failure, weak offspring, reduced milk yield, mastitis, abnormal respiration, reduced growth rate and even hairless offspring. The traditional toxicity symptoms of iodine in animals are anorexia, excess salivation, nasal or ocular discharge, abortion, pneumonia, and bone/tendon deformities. Furthermore, excessive feeding of ethylenediamine dihydoiodide (EDDI) is known to interfere with Vitamin A metabolism. High dietary calcium nitrate, thiocyanate, glucosinolate, perchlorate, rubidium and cobalt interfere with iodine metabolism and can increase iodine requirements. Metal iron for nutrient use does reduce iodine toxicity, but can also increase the need for iodine requirements.

It can be seen therefore that the conventional now used iodine sources in animal feed, such as inorganic iodine salts or amine salts all have their unique problems. There is therefore a continuing need for the development of unique iodine sources that provide better availability to the animal, that is, higher blood serum levels without simply adding more iodine. The primary objective of the present invention is to meet this need by providing organic trace mineral metal complexes of iodine, particularly with amino acid metal complexes, and most particularly with naturally occurring amino acids and/or essential amino acid metal complexes.

Lysine is an essential amino acid in the diet of mammals. That is, lysine cannot be synthesized by mammals at a rate adequate to meet the metabolic requirements, and so it must be supplied in the diet. Corn is notoriously low in lysine, and if used for animals in a single grain ration requires lysine supplementation both to maintain animal health and to achieve economic animal growth. Protected lysine molecules are a subject of commonly owned U.S. Pat. Nos. 7,704,521 and 7,846,471. As explained below, preferred compounds of the present invention providing enhanced bioavailability of iodine by providing two iodine ions per molecule and are those made from lysine reacted with a compound such as zinc to make lysine zinc diiodide (structure I, below).

The method of achieving the above primary objective as well as others will become apparent from the detailed description of the invention. It is understood that the invention is not limited by its primary objective and that other advantages of the invention such as efficiency of synthesis, lower cost of iodine, blood serum level iodine enhancement, i.e., bioavailability, and cost effectiveness of nutritional supplementation are all also achieved.

SUMMARY OF THE INVENTION

Metal amino acid iodide molecules, preferably metal lysine diiodides having one iodine moiety associated with the metal atom and the second associated with the amine salt are prepared and used to provide enhanced bioavailable iodine supplementation of animals (livestock and poultry) with increased blood serum levels of iodine resulting.

DETAILED DESCRIPTION OF THE PREFERRED EMBODIMENTS

In the ruminant animal, ingested feed first passes into the rumen where it is partially broken down by bacterial fermentation. During rumen fermentation, rumen microbes utilize nitrogen from nitrogen compounds that they have degraded to form microbial protein. Nitrogen sources for rumen microbes include rumen degradable protein and peptides, free amino acids and urea. Microbial protein and undegraded feed protein pass to the abomasum and small intestine where hydrochloric acid and mammalian enzymes degrade microbial protein and undegraded feed protein to free amino acids and short peptides. The amino acids and short peptides are absorbed in the intestine, and the ruminant animals utilize the amino acids for synthesis of protein to sustain life, grow, reproduce and produce milk.

Of the twenty or more amino acids utilized by the animal to synthesize proteins, nine are considered to be essential. Examples of the essential amino acids include leucine, isoleucine, valine, methionine, threonine, lysine, histidine, phenylalanine and trytophan. Essential amino acids are those amino acids which are required in quantities exceeding amounts produced by the animal, and must be supplied by microbial protein or rumen undegraded protein. Amino acids supplied in excess are degraded by the animal and excreted in the form of urea. The process of synthesizing urea from ammonia is a process requiring energy input from the animal. If certain essential amino acids are not provided in adequate amounts, the animal will be limited on the amount and types of protein it can produce, thus limiting animal performance. Supplying the proper amounts of essential amino acids therefore maximizes animal performance while enhancing efficiency of energy utilization by the animal.

Lysine and methionine are two of the most limiting essential amino acids when corn-based rations are fed. Results from studies also indicate that milk protein content is the most sensitive of the production variables (yield of milk, fat-corrected milk, milk protein, milk fat, and content of milk fat and protein) to alterations in amino acid content of duodenal digesta. Researchers have determined, by infusing incremental amounts of the limiting amino acids into the duodenum of lactating dairy cows, that the required contribution of lysine and methionine to total essential amino acids in duodenal digesta for maximum milk protein content approximated 15% and 5.2%, respectively.

The present invention relates to certain iodine complexes which provide to the animal (livestock or poultry) supplementation that provides both the opportunity for essential amino acid supplementation, iodine supplementation, and also provides a trace mineral. To the Applicant's present knowledge, there have been no compounds which have in the past provided all of these supplementations in the same compound. This is important because often times space in an animal feed mixture is an issue; and this invention fulfills three nutritional requirements with one molecule, with a net result of enhanced bioavailability of the iodine in the blood serum in comparison with normal sources of iodine, such as EDDI and calcium iodate.

The most preferred amino acid for use in the present invention is lysine to provide compounds such as zinc lysine diiodide of the formula:

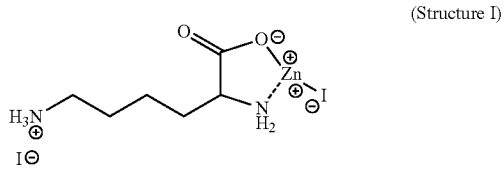

(Structure I)

As can be seen from Structure I, the iodine is provided in this compound at two sources; first, in association with the zinc atom and secondly in the iodine amine salt form. There is thus an opportunity of "double enhancement" with this compound. To say it another way, the structure has both amine salt iodine and a metal salt with iodine. The Structure I for the lysine diiodides can be generalized replacing the zinc atom with M representing the metal ion. For the present invention, suitable metal ions can be manganese and iron in case the generalized formula would be:

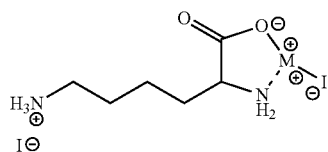

(Generalized formula for metal diiodide lysine salts - Structure II)

As heretofore mentioned, lysine is the preferred amino acid but not the only one which may be employed in the present invention. M can be zinc, manganese or iron. In fact, the invention may be generalized to other naturally occurring amino acids as follows:

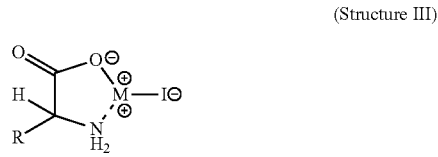

(Structure III)

In Structure III in the formula above, M represents the metal ion and can be zinc manganese or iron. R represents any remaining portion of a naturally occurring amino acid and can be selected from the group derived from essential amino acids including leucine, isoleucine, valine, methionine, threonine, lysine, histidine, phenylalanine and trytophan. The amino acid can also be one of the other 20 or more amino acids utilized by animals to synthesize proteins and also be a mixture of a variety of amino acids leading to a mixture of amino acid iodine metal salts (see Example II below).

It should be noted that in Structure (III) the amino group may be replaced with a hydroxy to form hydroxyl acid metal complexes with iodine. Put another way to generalize, the amino group of Structure (III) can be replaced with "X", and "X" can be either amino or hydroxyl. Other possibilities include R is $CH_3$, R is H, R is $C_2H_5$, and R is $C_2H_4SCH_3$, in which case the acid is respectively lactic acid, glycolic acid, hydroxybutyric acid and hydroxy-methylthio-butyric acid (see Example III).

The process of preparation of the amino acid metal iodide salts is straight forward, simply mixing equimolar amounts in an aqueous medium of the amino acid and the source of the metal ion, for example if its zinc, zinc iodide. It is stirred and heated for a time sufficient to allow the reaction to occur, preferably around 100° C. for 30-40 minutes. This is followed by cooling to room temperature, drying to leave a solid which if not powdered is ground to produce a powder material. It can be dried by spraying or rotary evaporation drying, etc. One of the efficiencies providing for cost effectiveness is the simple methodology for preparation.

The compounds prepared as above, and especially those listed as preferred, are easily processable. They can be sold pure as a supplementing additive or they can be mixed with carriers to improve packaging, processability, and taste. Preferred carriers are, for example, powdered sugar which significantly improves taste for the ruminants that ingest the same. For example, the Benzaldehyde derivatives have an almond taste which can be masked with powdered sugar.

The compounds can also be used as a part of the overall trace mineral supplementation for the animal.

While it is preferred that the compounds of the present invention be added without additional carriers or filler material, as heretofore mentioned flavorants can be used as or with the carrier. If carriers are employed, the carrier can be suitable carriers such as distillers fermentation solubles, feed grains, corn cob flour, whey, or other cellulosic carrier materials. They can also be added at the same time or with other trace mineral preparations.

The amount of supplement added to the feed ration will vary, of course, depending on whether one is using the pure compositions or the composition with a carrier. Basically the supplement will simply mix with the feed ration, as sold.

Generally the compounds should be added at a level to provide sufficient essential Iodine for the animals performance levels and daily nutritional needs, i.e., within the range of about 25 mg/head/day to about 50 milligrams per animal per day for performance level and 5-10 mg/day for nutrition level. Thus, the overall range of addition is from 5 mg to 50 mg per head per day, depending upon objective.

The following examples are offered to further illustrate but not limit of the invention compounds and how to show their use for effective enhancement of iodine supplementation in livestock or poultry at the blood serum level.

EXAMPLE I

Synthesis of Zinc Lysine Diiodide (Structure I)

Lysine (4.24 gr, 0.029 moles) was dissolved in water (200 mL). To this solution was added $ZnI_2$ (9.26 gr, 0.29 moles). This mixture was stirred and heated to 100 C for 35 minutes. This solution was allowed to cool to room temperature and the resulting solution was dried by rotary evaporation resulting in an off white solid. The material was analyzed for zinc content and iodine content. Zinc percentage 12.8 and Iodine percentage 50.5.

EXAMPLE II

Synthesis of Zinc (Amino Acid) Iodide (Structure III with Mixed Amino Acids and M=Z)

A mixture of amino acids was prepared by blending the following amino acids:

| Amino Acid | MW | Weight |
|---|---|---|
| ARG | 174.20 | 7.22 |
| ASP | 133.10 | 7.32 |
| CYS | 240.30 | 1.14 |
| GLU | 147.13 | 11.88 |
| GLY | 75.07 | 9.31 |
| HIS | 209.63 | 0.84 |
| LEU | 131.20 | 8.52 |
| LYS | 182.65 | 1.97 |
| MET | 149.20 | 2.63 |
| PRO | 115.13 | 7.35 |
| SER | 105.09 | 12.26 |
| TYR | 181.19 | 3.06 |
| VAL | 117.15 | 6.76 |
| Total AA | | 80.26 gr |

This amino acid mixture has an average molecular weight of 130.57

10.2 gr of this amino acid mixture (0.078 moles) was dispersed in 250 mL of water and $ZnI_2$ (24.9 gr, 0.078 moles) was added. This mixture was heated until it was a solution. This solution was then heated to 100° C. for 28 minutes. The mixture was cooled to room temperature and the water removed by rotary evaporation. The resulting product had 13.9 percent zinc and 53.2 percent iodine.

EXAMPLE III (Zinc hydroxy-methylthio-butyric Acid Iodide) (Structure III, M=Z and R is from Methionine Hydroxyl methylthio butanoic acid (88% solution) (35.7 gr, 0.21 moles) was dissolved in 350 mL of water. To this mixture was added $ZnI_2$ (67 gr, 0.21 moles). This mixture was stirred and the pH adjusted to pH=3 by the addition of 10N NaOH dropwise. The mixture was heated for 1.5 hours at 100° C. The resulting mixture was cooled and then dried down to a solid by rotary evaporation. This solid analyzed for 11.9% zinc and 30% iodine.

EXAMPLE IV (Zinc Glycine Iodide) (Structure III, M=Zn and R is from Glycine)

Glycine (28.6 gr, 0.381 moles) was dissolved in 150 mL of water. To this mixture was added $ZnI_2$ (121.6 gr, 0.381 moles) and the entire solution stirred and heated to 100° C. for 45 minutes. The mixture is cooled to room temperature and the solvent removed by rotary evaporation. The solid is analyzed for zinc and iodine. The dried product is analyzed for 14.3% zinc and 40% iodine.

EXAMPLE V

Synthesis of Iron Lysine Diiodide

Lysine (4.76 gr, 0.0326 moles) was dissolved in water (100 mL). To this solution was added $FeI_2$ (10.1 gr, 0.0326 moles). This mixture was stirred and heated to 100° C. for 35 minutes. This solution was allowed to cool to room temperature and the resulting solution was dried by rotary evaporation resulting in a brown solid. The material was analyzed for iron content and iodine content. Iron percentage 11.7% and Iodine percentage 53.4%.

EXAMPLE VI

Synthesis of Manganese Lysine Diiodide

Lysine (4.7 gr, 0.0323 moles) was dissolved in water (100 mL). To this solution was added $MnI_2$ (10.1 gr, 0.0323 moles). This mixture was stirred and heated to 100° C. for 35 minutes. This solution was allowed to cool to room temperature and the resulting solution was dried by rotary evaporation resulting in an off white solid. The material was analyzed for zinc content and iodine content. Manganese percentage 11.6% and Iodine percentage 52.1%.

EXAMPLE VII

This example illustrates the enhanced blood serum levels of iodine, demonstrating the superiority over conventional sources.

EDDI=ethylenediamine dihydroiodide $CaIO_3$=Calcium Iodate

Angus Simmental, nonlactating, pregnant beef cows, weighing between 1200 and 1700 lbs were assigned to a study with a completely randomized block design to determine the effect of novel iodine compounds on serum iodine concentration as compared to EDDI and $CaIO_3$. Cows were blocked on body weight at 7 days before the start of the trial. Cows were fed a bolus containing 60 mg of iodine from the various sources from day 0-day 10. Blood serum iodine was measured and reported as an average of day 2-14 and as a peak value at day 10. Compounds 1 and 2 showed higher blood levels of iodine than $CaIO_3$ or EDDI.

60 mg Iodine/day for 10 days

| | 60 mg Iodine/day for 10 days | |
|---|---|---|
| Treatment | Average Serum iodine level (day 2-day 14) | Day 10 (last treatment day) |
| No Iodine | 35 | 34 |
| EDDI | 141 | 274 |
| $CaIO_3$ | 148 | 290 |
| Structure I | 184 | 380 |
| Structure II | 173 | 348 |

EXAMPLE VIII

In another efficacy trial, Angus Simmental, nonlactating, pregnant beef cows, weighing between 1200 and 1700 lbs were assigned to a study with a completely randomized block design to determine the effect of novel iodine compounds as compared to EDDI and $CaIO_3$ on serum iodine concentration. Cows were blocked on body weight at 7 days before the start of the trial.

60 mg Iodine/day for 10 days

| Treatment | Average Serum iodine level (day 2-day 14) | Day 10 (last treatment day) |
|---|---|---|
| No Iodine | 94 | 86 |
| EDDI | 233 | 341 |
| CaIO$_3$ | 227 | 359 |
| Compound of Example III | 386 | 630 |
| Compound of Example IV | 380 | 637 |

As can be seen from the above examples, the metal amino acid bound iodine is producing a much higher blood serum level of iodine than the standard (EDDI, CaIO$_3$) materials, indicating enhanced bioavailable levels of iodine.

Similar results are achieved if the metal is manganese or iron, and if other naturally occurring amino acids are employed, singly or in combination.

What is claimed is:

1. A method of enhancing livestock and poultry iodine bioavailability from iodine nutrient sources, comprising: feeding animals a nutritional supplementation effective amount of a metal lysine diiodide of the formula:

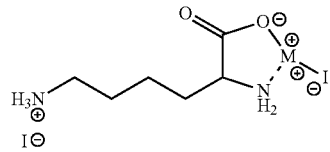

wherein M is a metal ion selected from the group consisting of zinc, manganese, and iron, said compound providing a higher blood serum iodine concentration than the same amount of standard iodine sources, ethylenediamine dihydroiodide (EDDI) and calcium iodate.

2. The method of claim 1 wherein the diet supplementing effective amount is an amount sufficient to provide a level of from about 5 milligrams per head per day to about 50 milligrams of iodine per head per day.

3. The method of claim 1 wherein the supplement is added in conjunction with non-toxic carriers.

4. The method of claim 3 wherein the non-toxic carriers are selected from the group consisting of sugars, fermentation solubles, feed grains, corn cob flour, and whey.

* * * * *